(12) United States Patent
Hill

(10) Patent No.: US 11,745,229 B2
(45) Date of Patent: Sep. 5, 2023

(54) ENDPOINT DETECTION OF DEPOSITION CLEANING IN A PUMPING LINE AND A PROCESSING CHAMBER

(71) Applicant: MKS Instruments, Inc., Andover, MA (US)

(72) Inventor: Gordon Hill, Andover, MA (US)

(73) Assignee: MKS Instruments, Inc., Andover, MA (US)

( * ) Notice: Subject to any disclaimer, the term of this patent is extended or adjusted under 35 U.S.C. 154(b) by 72 days.

(21) Appl. No.: 16/990,396

(22) Filed: Aug. 11, 2020

(65) Prior Publication Data

US 2022/0048081 A1 Feb. 17, 2022

(51) Int. Cl.
*B08B 9/027* (2006.01)
*G01N 21/31* (2006.01)
(Continued)

(52) U.S. Cl.
CPC .............. *B08B 9/027* (2013.01); *B08B 5/00* (2013.01); *B08B 9/08* (2013.01); *B08B 9/46* (2013.01);
(Continued)

(58) Field of Classification Search
CPC ........... H01J 37/32963; C23C 16/4405; B08B 9/027; B08B 2209/027
See application file for complete search history.

(56) References Cited

U.S. PATENT DOCUMENTS

| 5,637,279 A | 6/1997 | Besen et al. |
| 5,707,451 A | 1/1998 | Robles et al. |

(Continued)

FOREIGN PATENT DOCUMENTS

| EP | 2312612 | 4/2011 |
| GB | 2461816 A | 1/2010 |

(Continued)

OTHER PUBLICATIONS

Hur Min et al.• "AC Low-pressure Plasmas Generated by Using Annular-shaped Electrodes for Abatement of Pollutants Emitted during Semiconductor Manufacturing Processes". Journal of the Korean Physical Society, vol. 59, No. 4, Oct. 14, 2011, pp. 2742-2749.

(Continued)

*Primary Examiner* — Natasha N Campbell
(74) *Attorney, Agent, or Firm* — Cesari and McKenna, LLP

(57) ABSTRACT

A method is provided for cleaning of a processing system comprising a wafer processing chamber and a pumping line in fluid connection with the wafer processing chamber. The method includes initiating cleaning of the wafer processing chamber by activating a chamber cleaning source and initiating cleaning of at least a portion of the pumping line by activating a foreline cleaning source coupled to the pumping line. The method also includes monitoring, at a downstream endpoint detector coupled to the pumping line, a level of a signature substance. The method further includes determining, by the downstream endpoint detector, at least one of a first endpoint of the cleaning of the wafer processing chamber or a second endpoint of the cleaning of the pumping line based on the monitoring.

8 Claims, 6 Drawing Sheets

(51) Int. Cl.
*G01N 33/00* (2006.01)
*B08B 13/00* (2006.01)
*B08B 9/08* (2006.01)
*B08B 9/46* (2006.01)
*C23C 16/44* (2006.01)
*H01J 37/32* (2006.01)
*B08B 5/00* (2006.01)

(52) U.S. Cl.
CPC .......... *B08B 13/00* (2013.01); *C23C 16/4405* (2013.01); *G01N 21/31* (2013.01); *G01N 33/0036* (2013.01); *H01J 37/32963* (2013.01); *B08B 2209/027* (2013.01); *B08B 2209/08* (2013.01)

(56) References Cited

U.S. PATENT DOCUMENTS

| | | | |
|---|---|---|---|
| 5,812,403 A * | 9/1998 | Fong | C23C 16/4405 700/121 |
| 5,827,370 A | 10/1998 | Gu | |
| 6,156,667 A | 12/2000 | Jewett | |
| 6,187,072 B1 | 2/2001 | Cheung et al. | |
| 6,193,802 B1 | 2/2001 | Pang et al. | |
| 6,255,222 B1 | 7/2001 | Xia et al. | |
| 6,354,241 B1 | 3/2002 | Tanaka et al. | |
| 6,360,685 B1 | 3/2002 | Xia et al. | |
| 6,366,346 B1 | 4/2002 | Nowak et al. | |
| 6,517,786 B1 | 2/2003 | Best et al. | |
| 6,680,420 B2 | 1/2004 | Pang et al. | |
| 7,037,376 B2 | 5/2006 | Harvey et al. | |
| 7,060,234 B2 | 6/2006 | Pokharna et al. | |
| 7,494,628 B2 | 2/2009 | Pokharna et al. | |
| 7,964,040 B2 | 6/2011 | Rasheed et al. | |
| 8,747,762 B2 | 6/2014 | Dickinson et al. | |
| 8,852,520 B2 | 10/2014 | Hur et al. | |
| 9,314,824 B2 | 4/2016 | Gu et al. | |
| 9,472,381 B2 | 10/2016 | Hur et al. | |
| 9,597,634 B2 | 3/2017 | Dickinson et al. | |
| 9,649,592 B2 | 5/2017 | Cox et al. | |
| 9,867,238 B2 | 1/2018 | Cox et al. | |
| 10,115,571 B2 | 10/2018 | Dickinson | |
| 10,179,941 B1 | 1/2019 | Khan et al. | |
| 10,187,966 B2 | 1/2019 | Wang et al. | |
| 10,337,105 B2 | 7/2019 | Hill | |
| 10,535,506 B2 | 1/2020 | Hill et al. | |
| 11,024,489 B2 | 6/2021 | Hill et al. | |
| 2003/0007910 A1 | 1/2003 | Diamant Lazarovich et al. | |
| 2003/0027428 A1 * | 2/2003 | Ng | H01J 37/32963 438/706 |
| 2004/0001787 A1 | 1/2004 | Porshnev et al. | |
| 2004/0131513 A1 | 7/2004 | Lazarovich et al. | |
| 2005/0011445 A1 | 1/2005 | Upham | |
| 2005/0194099 A1 | 9/2005 | Jewett, Jr. et al. | |
| 2006/0107973 A1 | 5/2006 | Leung | |
| 2006/0207630 A1 | 9/2006 | Sakai et al. | |
| 2007/0095282 A1 | 5/2007 | Moon et al. | |
| 2007/0286766 A1 | 12/2007 | Choi | |
| 2008/0057726 A1 | 3/2008 | Kim | |
| 2009/0196765 A1 | 8/2009 | Dyer et al. | |
| 2010/0192542 A1 | 8/2010 | Min et al. | |
| 2011/0089017 A1 | 4/2011 | Hur et al. | |
| 2011/0272592 A1 | 11/2011 | Kellogg et al. | |
| 2013/0087287 A1 | 4/2013 | Hur et al. | |
| 2013/0133697 A1 * | 5/2013 | Stockman | B08B 7/0035 134/22.1 |
| 2013/0146225 A1 | 6/2013 | Chen et al. | |
| 2013/0164943 A1 * | 6/2013 | Koshi | C23C 16/455 118/712 |
| 2015/0129047 A1 | 5/2015 | Gu et al. | |
| 2015/0252472 A1 | 9/2015 | Ko et al. | |
| 2015/0252473 A1 | 9/2015 | Dickinson | |
| 2015/0314233 A1 | 11/2015 | Hur et al. | |
| 2017/0173521 A1 | 6/2017 | Dickinson et al. | |
| 2017/0200591 A1 * | 7/2017 | Hill | H01J 37/32963 |
| 2017/0221683 A1 | 8/2017 | Kim et al. | |
| 2020/0286712 A1 | 9/2020 | Polak et al. | |
| 2021/0082672 A1 | 3/2021 | Hill et al. | |

FOREIGN PATENT DOCUMENTS

| | | |
|---|---|---|
| JP | H11222680 A | 8/1982 |
| JP | H0226804 A | 1/1990 |
| JP | H08-183107 | 7/1996 |
| JP | 10168574 | 6/1998 |
| JP | H11222680 A | 8/1999 |
| JP | 2005175460 A | 6/2005 |
| JP | 2005303255 A | 10/2005 |
| JP | 2010234195 A | 10/2010 |
| JP | 2010247126 A | 11/2010 |
| JP | 2011511615 A | 4/2011 |
| JP | 2013-519188 | 5/2013 |
| JP | 2013089537 A | 5/2013 |
| JP | 2014520385 A | 8/2014 |
| JP | 2015-213171 A | 11/2015 |
| KR | 1020090028991 A | 3/2009 |
| KR | 101063515 B1 | 9/2011 |
| WO | 00/51714 A1 | 9/2000 |
| WO | 2009097068 A1 | 8/2009 |
| WO | 2009097068 A1 | 8/2011 |
| WO | 2011092186 A1 | 8/2011 |
| WO | 2014-062006 A1 | 4/2014 |
| WO | 2015160057 A1 | 10/2015 |
| WO | 2015181945 A1 | 12/2015 |
| WO | 2015/181945 | 4/2017 |

OTHER PUBLICATIONS http://www.appliedmaterials.com/nanochip/nanochip-fab-solutions/july-2016/new-aeris-s-technology-helps-increase- subfab-safety-while-reducing-emissions, 6 pages, Accessed: Oct. 1, 2019.

http://www.appliedmaterials.com/products/aeris-si. 3 pages, Accessed: Oct. 1, 2019.

http://www.appliedmaterials.com/products/aeris-g-plasma-abatement-system. 5 pages, Accessed: Oct. 1, 2019.

"European Search Report, and Written Opinion," European Application No. 22195361.5-1211, Applicant: MKS Instruments, Inc., dated Jan. 9, 2023, pp. 1-11.

"Notification of Transmittal of the International Search Report and the Written Opinion of the International Searching Authority, or the Declaration," International Filing Date: Jul. 26, 2022, International Application No. PCT/US2022/074132 Applicant: MKS Instruments, Inc., dated Nov. 14, 2022, pp. 1-10.

* cited by examiner

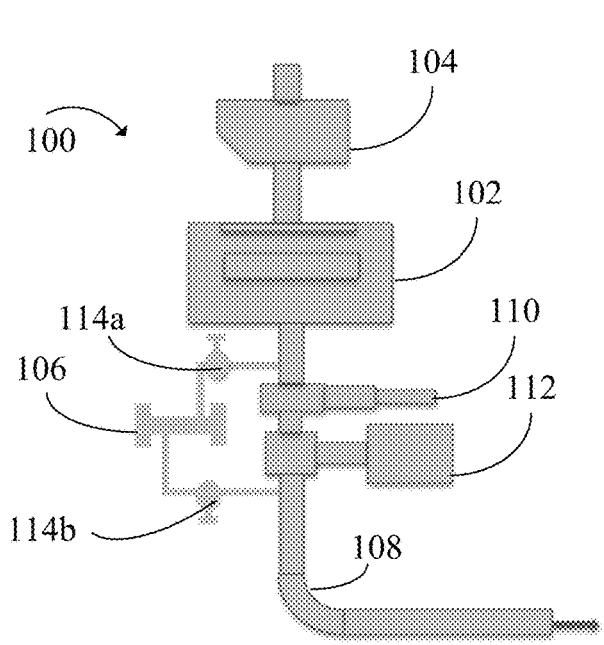
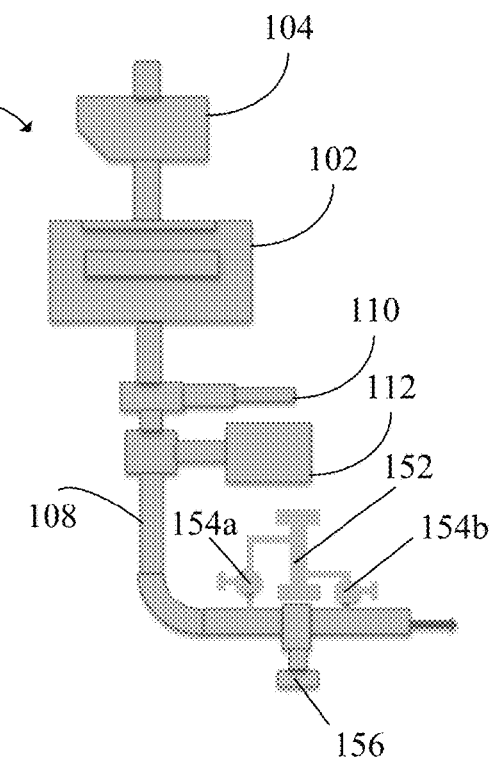
FIG. 1a (Prior Art)
FIG. 1b (Prior Art)
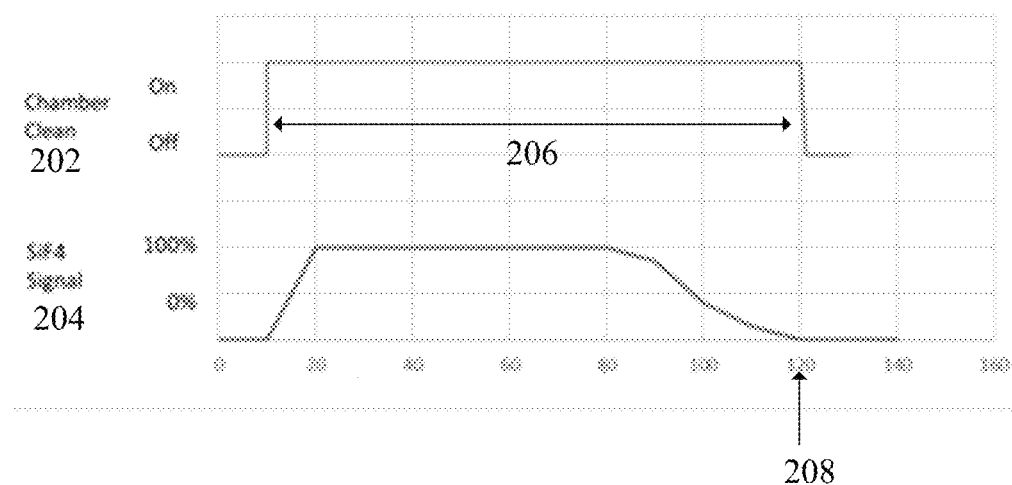
FIG. 2 (Prior Art)

ENDPOINT DETECTION OF DEPOSITION CLEANING IN A PUMPING LINE AND A PROCESSING CHAMBER

FIELD OF THE INVENTION

The invention generally relates to cleaning of a processing system that includes a wafer processing chamber and a vacuum pumping line in a semiconductor processing environment.

BACKGROUND

Deposition processes, including chemical vapor deposition (CVD) processes, are commonly used in the manufacturing of semiconductor devices. For example, in a typical CVD process, reactant gases are introduced into a wafer processing chamber and directed to a heated substrate to induce controlled chemical reactions, which result in the deposition of a thin film on the surface of the substrate. During the deposition process, chamber pressure is precisely controlled by one or more mechanical devices, such as vacuum valves, connected downstream from the wafer processing chamber. For example, an isolation valve is typically connected directly to the exhaust gas port of the wafer processing chamber, a throttle valve is situated downstream from the isolation valve, and a vacuum pump is located further downstream from both of the isolation and throttle valves. The plumbing between the wafer processing chamber and the vacuum pump (e.g., the pipelines and valves) is generally referred to as a foreline, a roughing line or a vacuum pumping line.

During a deposition process, the throttle valve can cycle between open and closed positions to regulate the gas pressure inside of the wafer processing chamber. Most of the material produced from the reactant gases is deposited on the substrate surface in the chamber. However, some material is also deposited on surfaces downstream from the chamber, such as on the throttle valve. As unwanted material accumulates on the throttle valve, the throttle valve's useful life can be reduced by, for example, introduction of seal wear, load addition, requirement for high torque drive systems, and alteration of conductance characteristics. Ultimately, unwanted material deposits on a throttle valve diminish the precise operation of the valve, thereby reducing the valve's ability to control gas pressure inside of the wafer processing chamber. Other vacuum valves along the vacuum pumping line can be similarly affected by unwanted material deposition. In addition, the position of a throttle valve during closed loop pressure control can provide useful diagnostic information. However, because valve position varies with quantity of deposition, unwanted deposition on a valve can limit the usefulness of valve positioning as an indication of other changes in the system.

Further, during a wafer deposition process, unwanted material produced from the reactant gases can be deposited along the vacuum pumping line as the reactant gases are pumped out from the processing chamber through the pumping line. Similar to the throttle valve, accumulation of the unwanted material in the vacuum pumping line can produce a host of problems, including clogging the pumping line and other downstream equipment, interfering with normal operation of the associated vacuum pump, reducing the vacuum pump's useful life, and contaminating processing steps in the processing chamber.

Existing systems and methods are available for cleaning the wafer processing chamber and/or the vacuum pumping line. For example, an inline plasma source for cleaning at least a portion of a vacuum pumping line is described by U.S. Pat. No. 10,535,506 assigned to MKS Instruments, Inc. of Andover, Mass., the contents of which are hereby incorporated herein by reference. Various cleaning techniques for wafer processing chambers are also known, as well as endpoint detection approaches that provides an indication of the end of cleaning of a wafer processing chamber, where the clean time can be variable. FIGS. 1a and 1b show prior art chemical vapor deposition (CVD) systems 100, 150 with chamber cleaning and endpoint detection capabilities. As shown in FIG. 1a, the system 100 includes a processing chamber 102 and a remote plasma source 104 installed upstream from processing chamber 102. The remote plasma source 104 is adapted to generate a stream of reactive cleaning gas (e.g., atomic fluorine) that flows into the processing chamber 102 to clean the chamber 102. An endpoint detector 106 can be positioned downstream from processing chamber 102 and coupled to a vacuum pumping line 108 of the system 100. For example, the endpoint detector 106 can be mounted onto a bypass on the pumping line 108 such that it is parallel to a gate valve 110 and a throttle valve 112 on the pumping line 108. The endpoint detector 106 is configured to monitor the level of a signature chemical substance in the pumping line 108 that is produced by the cleaning operation initiated at the remote plasma source 104. As shown, the endpoint detector 106 can be positioned between a pair of endpoint bypass valves 114a, 114b on the bypass to allow isolation of the endpoint detector 106 during a deposition process, so that components inside of the endpoint detector 106, such as optical components, are not contaminated. FIG. 1b shows an alternative implementation of the system 100 of FIG. 1a. In this system 150, an endpoint detector 152 and associated bypass valves 154a, 154b are located downstream of the gate valve 110 and the throttle valve 112. Optionally, a bypass valve 156 can be located parallel to the endpoint detector 152 to force the gas flow through the endpoint detector 152 during a cleaning operation so as to optimize detection response time of the endpoint detector 152. The monitored data produced by the endpoint detector 106 of FIG. 1a or by the endpoint detector 152 of FIG. 1b can be used to determine when an endpoint of the chamber cleaning operation is reached, such as by comparing the level of the signature chemical substance to a predefined endpoint threshold level. The signature chemical substance can be silicon tetrafluoride ($SiF_4$), for example. FIG. 2 shows a set of exemplary signals produced by the prior art CVD system of FIG. 1a or FIG. 1b. As shown, signal 202 is a binary signal that represents the state of a chamber cleaning operation (e.g., on or off) by the remote plasma source 104 of FIG. 1a or FIG. 1b. Signal 204 represents the level of a signature chemical substance in the pumping line 108 measured at the endpoint detector 106 of FIG. 1a or the endpoint detector 152 of FIG. 1b. For example, the endpoint detector 106 or the endpoint detector 152 can measure the partial pressure of $SiF_4$ in the pumping line 108 during the cleaning operation. As shown, the lowering of the partial pressure measurement toward the end of a cleaning period 206 signals that the processing chamber 102 of FIG. 1a or FIG. 1b is relatively clean. Specifically, once the partial pressure measurement of $SiF_4$ reaches a threshold level, such as about 0%, which is shown in FIG. 2 as around time point 208, the remote plasma source 104 can be deactivated to turn off the chamber cleaning operation. One shortcoming associated with the prior art systems 100, 150 is that they are only designed to detect the endpoint of a cleaning process associated with the processing chamber 102. The systems do not accommodate cleaning of the pumping line 108, which can also accumulate unwanted material as described above, or incorporate any endpoint detection mechanism for pumping line cleaning in conjunction with processing chamber cleaning.

Further, in many cases chamber cleaning is performed with a fixed time recipe and endpoint detection is not utilized. Applying such an open-looped, fixed-time based cleaning procedure (without endpoint detection) for vacuum pumping line cleaning is problematic as the rate and amount of deposition accumulating in a vacuum pumping line is not well studied and is typically not well quantified, which makes it difficult to predict what cleaning duration is required. Due the complexities that exist in a semiconductor processing environment, a uniform time cannot address all chamber cleaning and/or pumping line cleaning requirements. Thus, there is a need for endpoint detection methods and apparatus in a semiconductor processing system equipped for both wafer processing chamber cleaning and pumping line cleaning. For such a combined cleaning system, it is desirable to be able to dynamically detect the end of one or both of a chamber cleaning operation and a pumping line cleaning operation.

SUMMARY

The present invention features systems and methods that provide dynamic endpoint detection for a semiconductor processing system equipped for both wafer processing chamber cleaning and pumping line cleaning, where the processing chamber and the pumping line have different cleaning sources (i.e., do not share the same cleaning source). Systems and methods of the present invention integrate both chamber cleaning and pumping line cleaning in one processing environment as well as provide endpoint detection for one or both types of cleaning. In some embodiments, measurements of the partial pressure of a signature chemical substance, such as silicon tetrafluoride ($S_fF_4$), is used by one or more endpoint detectors of the system for monitoring cleaning performance in the wafer processing chamber and/or the pumping line.

In one aspect, a method is provided for cleaning of a processing system comprising a wafer processing chamber and a pumping line in fluid connection with the wafer processing chamber and located downstream from the wafer processing chamber. The method includes initiating cleaning of the wafer processing chamber by activating a chamber cleaning source and initiating cleaning of at least a portion of the pumping line by activating a foreline cleaning source coupled to the pumping line. The foreline cleaning source is located downstream from the wafer processing chamber. The method also includes monitoring, at a downstream endpoint detector coupled to the pumping line, a level of a signature substance. A location of the downstream endpoint detector is downstream from both the wafer processing chamber and the foreline cleaning source. The method further includes determining, by the downstream endpoint detector, at least one of a first endpoint of the cleaning of the wafer processing chamber or a second endpoint of the cleaning of the pumping line based on the monitoring.

In another aspect, a method is provided for cleaning of a processing system comprising a wafer processing chamber and a pumping line in fluid connection with the wafer processing chamber and located downstream from the wafer processing chamber. The method includes initiating cleaning of the wafer processing chamber by activating a chamber cleaning source and initiating cleaning of at least a portion of the pumping line by activating a foreline cleaning source coupled to the pumping line. The foreline cleaning source is located downstream from the wafer processing chamber. At least a portion of a duration of the cleaning of the pumping line overlaps in time with at least a portion of a duration of the cleaning of the wafer processing chamber. The method also includes monitoring, at an intermediate endpoint detector coupled to the pumping line, a first level of a signature substance to determine a first endpoint of the cleaning of the wafer processing chamber. A location of the intermediate endpoint is downstream from the wafer processing chamber. The method further includes monitoring, at a downstream endpoint detector coupled to the pumping line, a second level of the signature substance to determine a second endpoint of the cleaning of the pumping line. A location of the downstream endpoint detector is downstream from the wafer processing chamber, the foreline cleaning source and the intermediate endpoint detector.

In yet another aspect, a processing system is provided that includes a wafer processing chamber, a pumping line in fluid connection with the wafer processing chamber and located downstream from the wafer processing chamber, means for cleaning the wafer processing chamber and means for cleaning at least a portion of the pumping line. The means for cleaning the pumping line is coupled to the pumping line and located downstream from the wafer processing chamber. Activation of the means for cleaning the wafer processing chamber overlaps for at least a portion in duration with activation of the means for cleaning the pumping line. The system also includes monitoring means, coupled to the pumping line, for monitoring a level of a signature substance at a location that is downstream from both the wafer processing chamber and the means for cleaning the pumping line. The system further includes means for determining at least one of a first endpoint of cleaning of the wafer processing chamber or a second endpoint of cleaning of the pumping line based on the monitoring.

Any of the above aspects can include one or more of the following features. In some embodiments, the downstream endpoint detector determines at least one of the first or second endpoint by detecting when the level of the signature substance decays to a predetermined threshold. In some embodiments, the signature substance comprises silicon tetrafluoride ($S_fF_4$).

In some embodiments, the chamber cleaning source is located upstream and remote from the wafer processing chamber. The chamber cleaning source can comprise a plasma source. In some embodiments, the foreline cleaning source comprises an inline plasma source. The inline plasma source can generate a localized plasma using a cleaning gas supplied to the pumping line via the wafer processing chamber to clean the at least portion of the pumping line.

In some embodiments, the downstream endpoint detector is adapted to detect the first endpoint and the second endpoint when both the chamber cleaning source and the foreline cleaning source remain activated until the level of the signature substance decays to a predefined threshold. In some embodiments, the downstream endpoint detector is adapted to detect the first endpoint of the cleaning of the wafer processing chamber when the foreline cleaning source is deactivated prior to the chamber cleaning source.

In some embodiments, an intermediate endpoint detector coupled to the pumping line is configured to monitor a second level of the signature substance. In some embodiments, a location of the intermediate endpoint detector is downstream from the wafer processing chamber while upstream from the foreline cleaning source and the downstream endpoint detector. The intermediate endpoint detector can detect the first endpoint of the wafer processing chamber cleaning based on the second level of the signature substance monitored. Further, a difference between the level of the signature substance monitored by the downstream endpoint detector and the second level of the signature substance monitored by the intermediate endpoint detector can be used to detect the second endpoint of the pumping line cleaning.

In some embodiments, the location of the intermediate endpoint detector is downstream from the wafer processing chamber and the foreline cleaning source, while upstream from the downstream endpoint detector. In this configuration, the foreline cleaning source can be deactivated prior to monitoring by the intermediate endpoint detector to detect the first endpoint of the wafer processing chamber cleaning. In some embodiments, the level of the signature substance monitored by the downstream endpoint detector is used to detect the second endpoint of the pumping line cleaning.

In some embodiments, the downstream endpoint detector comprises a pair of isolation valves and a detection cell located therebetween.

In some embodiments, the foreline cleaning source is activated later than or at about the same time as activating the chamber cleaning source. In some embodiments, at least a portion of a duration of the cleaning of the pumping line overlaps in time with at least a portion of a duration of the cleaning of the wafer processing chamber.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the technology.

FIGS. 1a and 1b show prior art chemical vapor deposition (CVD) systems with chamber cleaning and endpoint detection capabilities.

FIG. 2 shows a set of exemplary signals produced by the prior art CVD system of FIG. 1a or FIG. 1b.

DETAILED DESCRIPTION

Figure 3:
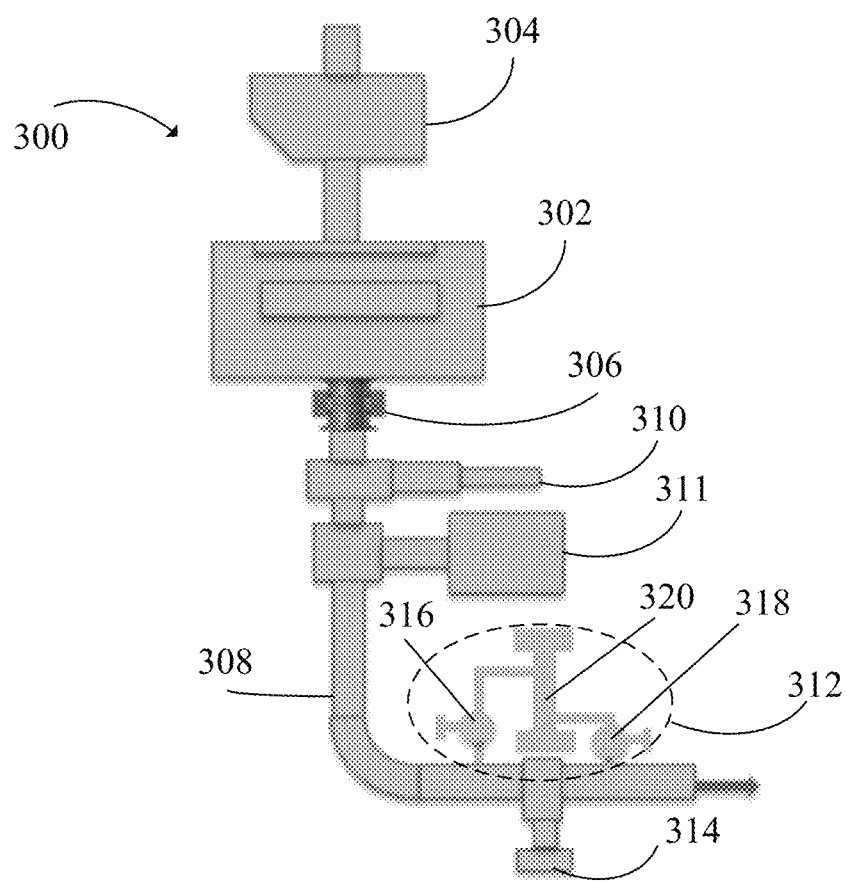
FIG. 3 shows an exemplary processing system with integrated chamber cleaning endpoint detection and pumping line cleaning endpoint detection, according to some embodiments of the present invention.

FIG. 3 shows an exemplary processing system 300 with integrated chamber cleaning endpoint detection and pumping line cleaning endpoint detection, according to some embodiments of the present invention. The processing system 300 can be a chemical vapor deposition system for a semiconductor processing environment, where the system 300 generally includes a wafer processing chamber 302 configured to process wafers in a deposition process and a vacuum pumping line 308 in fluid connection with the processing chamber 302 and located downstream from the processing chamber 302. The pumping line 308, which includes a gate valve 310 and a throttle valve 311, can connect the processing chamber 302 to a pump (not shown) of the system 300. The system 300 also includes a chamber cleaning source 304 configured to clean the processing chamber 302 after a deposition operation in the processing chamber 302. In FIG. 3, the chamber cleaning source 304 is shown to be located upstream and remote from the processing chamber 302. In alternative embodiments, the chamber cleaning source 304 can be another type of cleaning source, such as an integrated source that is incorporated in the processing chamber 302 to clean the chamber 302. The chamber cleaning source 304 can be a plasma source that is configured to generate a reactive gas by applying plasma to a cleaning gas and introduce the reactive gas to the processing chamber 302 to react with surface films in the chamber 302 for cleaning purposes, from which a byproduct signature chemical substance is produced. The cleaning gas supplied to the chamber cleaning source 304 can be a fluorinated or chlorinated gas (i.e. $NF_3$, $CF_4$, $NF_3$ combined with $O_2$, $SF_6$, etc.). The reactive gas generated from the dissociation of the cleaning gas using plasma can be radical fluorine, which can etch away the unwanted deposits in the chamber surface. The byproduct of such cleaning can be in the form of a signature chemical substance, such as silicon tetrafluoride ($SiF_4$), which is a stable gas that can be easily removed from the system 300. In other embodiments, alternative chemistry are used and alternative signature substances are produced and monitored for the purpose of endpoint detection. For example, in a tungsten deposition system, the byproduct of the cleaning process (thus the signature substance to be monitored) is tungsten hexafluoride ($WF_6$). In other deposition systems, the cleaning gas may contain chlorine, in which case the byproduct and signature substance to be monitored may be silicon tetrachloride ($SiCl_4$).

Further, the system 300 includes a foreline cleaning source 306 configured to clean at least a section of the vacuum pumping line 308 of the system 300. The foreline cleaning source 306 is coupled to the vacuum pumping line 308 and located downstream from the processing chamber 302, but upstream to the gate valve 310 and the throttle valve 311 of the pumping line 308. As shown in FIG. 3, the foreline cleaning source 306 is configured as an inline plasma source by forming an inline connection with one or more pumping line segments. In some embodiments, the plasma source 306 is substantially the same as the inline plasma source described in U.S. Pat. No. 10,535,506. Such an inline plasma source can generate plasma along the surface of its cylindrical interior volume and use the plasma to dissociate a cleaning gas supplied to the pumping line 308 via an upstream entry point, such as via the processing chamber 302. The resulting reactive gas (e.g., radical fluorine) generated by the foreline cleaning source 306 cleans at least a portion of the pumping line 308, from which a signature chemical substance is generated. In alternative embodiments (not shown), the foreline cleaning source 306 is a remote cleaning source and the output of the remote plasma source is introduced into the pumping line 308 using a tee fitting. In this implementation, an isolation valve may be used between the remote plasma source and the pumping line 308. The cleaning gas used by the foreline cleaning source 306 can be the same as the cleaning gas supplied to the chamber cleaning source 304 (e.g., a fluorinated or chlorinated gas), from which the same reactive gas (e.g., radial fluorine) and signature chemical substance (e.g., $SiF_4$) is generated during the pumping line cleaning process.

Figure 4:
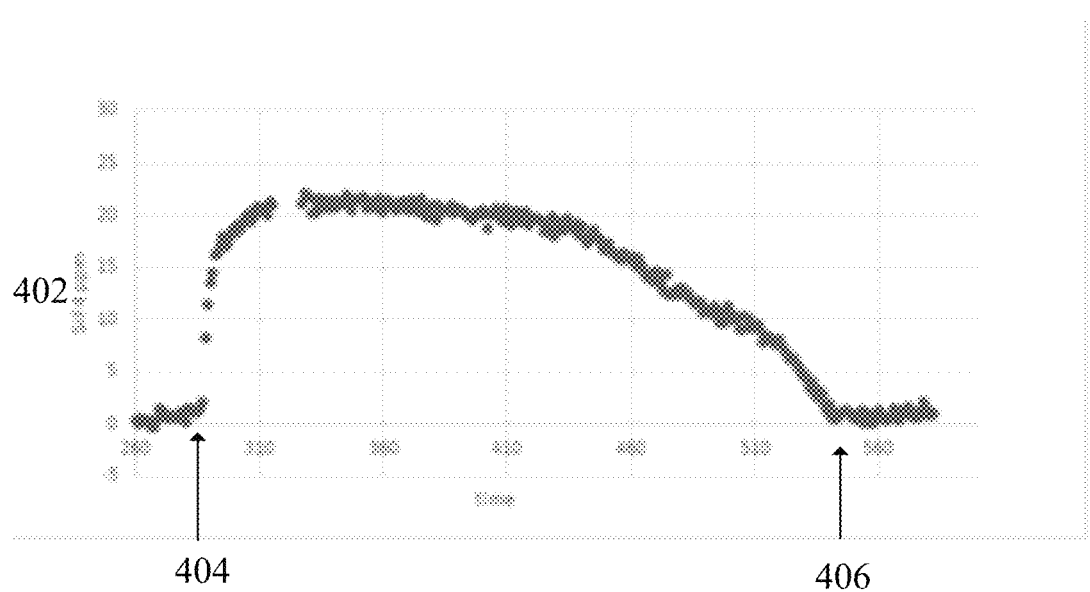
FIG. 4 shows an exemplary diagram of silicon tetrafluoride concentration during a cleaning operation by the foreline cleaning source of the processing system of FIG. 3, according to some embodiments of the present invention.

FIG. 4 shows an exemplary diagram of silicon tetrafluoride concentration 402 over a duration of a cleaning operation by the foreline cleaning source 306 of the processing system 300 of FIG. 3, according to some embodiments of the present invention. The foreline cleaning source 306 used to generate the data of FIG. 4 is an inline plasma source, the cleaning gas supplied to the inline plasma source 306 is nitrogen trifluoride ($NF_3$) with Argon, and the resulting reactive gas produced to etch away the unwanted silicon dioxide ($SiO_2$) samples on the pumping line 308 is atomic fluorine. As shown, at the start time 404 of the cleaning process, the concentration of the byproduct chemical substance generated from the cleaning reaction ($SiF_4$) increases due to the presence of the unwanted material in the pumping line 308. As the cleaning process progresses, the concentration of $SiF_4$ gradually decreases to a baseline level (e.g., about 0), which indicates most/all of the unwanted material is consumed, which signals that the endpoint 406 of the cleaning process is reached. In some embodiments, the concentration of $SiF_4$ reaches a steady state indicating that further changes are unlike to occur, which also signals the end of the cleaning process.

Referring back to FIG. 3, the processing system 300 also includes a downstream endpoint detector 312 coupled to the pumping line 308, where the downstream endpoint detector 312 is located downstream from both the processing chamber 302 and the foreline cleaning source 306. In some embodiments, the downstream endpoint detector 312 is downstream from the chamber cleaning source 304. In some embodiments, the downstream endpoint detector 312 is mounted onto a bypass on the pumping line 108 such that it is parallel to an optional endpoint bypass valve 314 of the pumping line 108. The optional endpoint bypass valve 314 is used to ensure that the gas flow is directed through the downstream endpoint detector 312 to optimize response time. The downstream endpoint detector 312 is configured to monitor a level of the signature chemical substance at its location on the pumping line 308. The signature chemical substance can be generated as a byproduct from a cleaning operation of the processing chamber 302 activated by the chamber cleaning source 304 and/or from a cleaning operation of the pumping line 308 activated by the foreline cleaning source 306, depending on the starting times and durations of these cleaning operations. In some embodiments, the same signature chemical substance (e.g., $SiF_4$) is generated from the two different cleaning operations.

In some embodiments, the downstream endpoint detector 312 performs such chemical detection/monitoring in real time or near real time by measuring the partial pressure of the signature chemical substance using infrared absorption. An exemplary configuration of the downstream endpoint detector 312 is shown in FIG. 3, where the detector 312 includes a pair of isolation valves 316, 318 with a detection cell 320 located therebetween. During a deposition operation, the isolation valves 314, 316 are closed so that no detection occurs. During a cleaning operation activated by the chamber cleaning source 304 and/or the foreline cleaning source 306, the valves 316, 318 are open such that the detection cell 318 can sample the gas flowing through the pumping line 308 at its location and detect a concentration of the signature chemical substance. In some embodiments, the endpoint detector 312 is configured to scan a slice of spectrum in the infrared region of the gas passing through and produce an absorption spectrum that is used to identify compounds of interest in the gas and provide their concentration values. For instance, the endpoint detector 312 can be a T Series Tunable Filter Spectrometer produced by MKS Instruments, Inc. Alternatively, the endpoint detector 312 can be configured to use other analysis techniques, including non-dispersive infrared (NDIR) analysis, residual gas analyzer (RGA), Fourier transform infrared spectroscopy (FTIR), and/or Optical Emission Spectroscopy (OES) to identify compounds of interest and their concentration values.

In some embodiments, the monitored data collected by the downstream endpoint detector 312 is used to determine at least one of an endpoint of cleaning of the processing chamber 302 or an endpoint of cleaning of the pumping line 308. It is well understood that the optimal cleaning time for a processing chamber is a complex function of a number of variables including thickness of the deposited material, temperature, pressure, reactive gas delivery and material chemical composition. Similar complexities are also associated with determining the optimal cleaning duration of the pumping line. Analysis of the data collected by the downstream endpoint detector 312 allows the system 300 to pinpoint in real time or near real time when cleaning processes of the processing chamber 302 and/or the pumping line 308 are completed, which is especially helpful when at least a portion of a duration of the cleaning of the pumping line 308 overlaps in time with at least a portion of a duration of the cleaning of the processing chamber 302.

Figure 5:
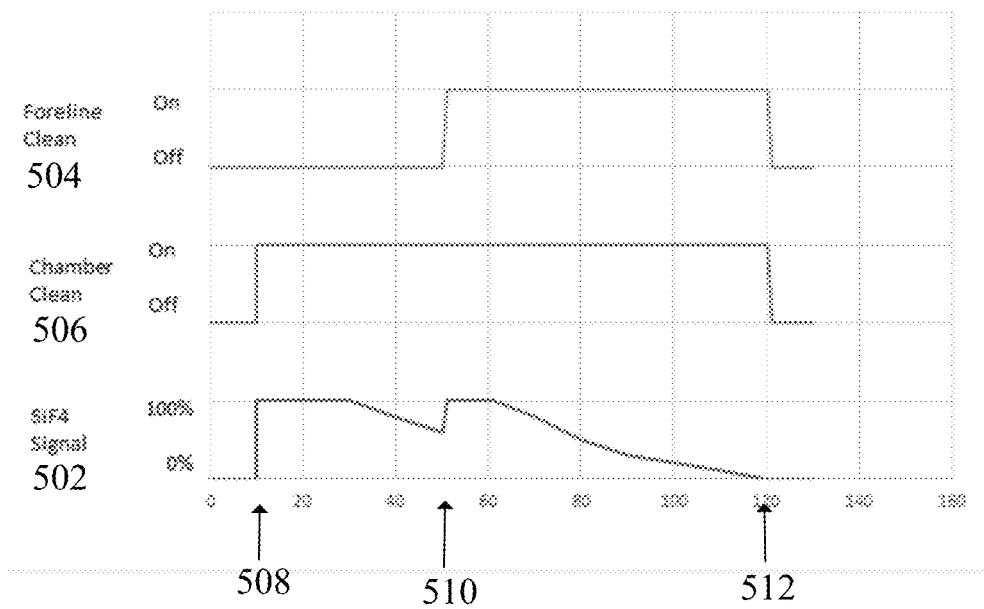
FIG. 5 shows an exemplary diagram of silicon tetrafluoride concentration measured by the endpoint detector of the processing system of FIG. 3, according to some embodiments of the present invention.

FIG. 5 shows an exemplary diagram of silicon tetrafluoride concentration 502 measured by the endpoint detector 312 of the processing system 300 of FIG. 3, according to some embodiments of the present invention. Specifically, the silicon tetrafluoride concentration 502 is measured over a duration 504 of a cleaning operation by the foreline cleaning source 306 and a duration 506 of a cleaning operation by the chamber cleaning source 304. In the exemplary operations of FIG. 5, the chamber cleaning source 304 activates the chamber cleaning operation at a start time 508, as reflected by the binary signal 506 being turned on at time 508. This corresponds to a sharp rise in the partial pressure of the byproduct signature chemical substance, $SiF_4$, detected by the endpoint detector 312, as reflected by the signal 502 at time 508. The start time of activation 510 of a pumping line cleaning operation by the foreline cleaning source 306 can be delayed relative to the start time 508 of chamber cleaning, as reflected by the binary signal 504 being turned on at the later time 510. In the cleaning approach depicted in FIG. 5, both chamber cleaning and pumping line cleaning remain active until the $SiF_4$ concentration measured at the endpoint detector 312 decays to a predetermined endpoint threshold, such as to about 0% partial pressure, at time 512, thus representing the end of cleaning of both the processing chamber 302 and the pumping line 308. Specifically, the downstream endpoint detector 312 measures the SiF4 concentration generated from the combination of chamber cleaning and pumping line cleaning and is able to detect the endpoints of both cleaning operations, as reflected by the signal 502 at time 512. In some embodiments, when the detector 312 determines that the endpoints are reached, the detector 312 can signal the system 300 to deactivate (i.e., turn off) both the chamber cleaning source 304 and the foreline cleaning source 306 in real time or near real time (e.g., around time 512).

In some embodiments, it is expected that the efficiency of pumping line cleaning is higher if the SiF4 content entering the foreline cleaning source 306 is lower, where the SiF4 content is generated by the upstream chamber cleaning operation. Thus, it can be advantageous to delay the start time 510 of the pumping line cleaning process in relation to the start time 508 of the chamber cleaning process, which allows pumping line cleaning to operate at higher efficiency. In some embodiments, a single signal from the system 300 controls activation of both chamber cleaning and pumping line cleaning, in which case the foreline cleaning source 306 can be configured to delay its plasma ignition for some configurable time after receipt of the central activation signal, while the chamber cleaning source 304 can start its cleaning operation immediately after receipt of the central activation signal.

Figure 6:
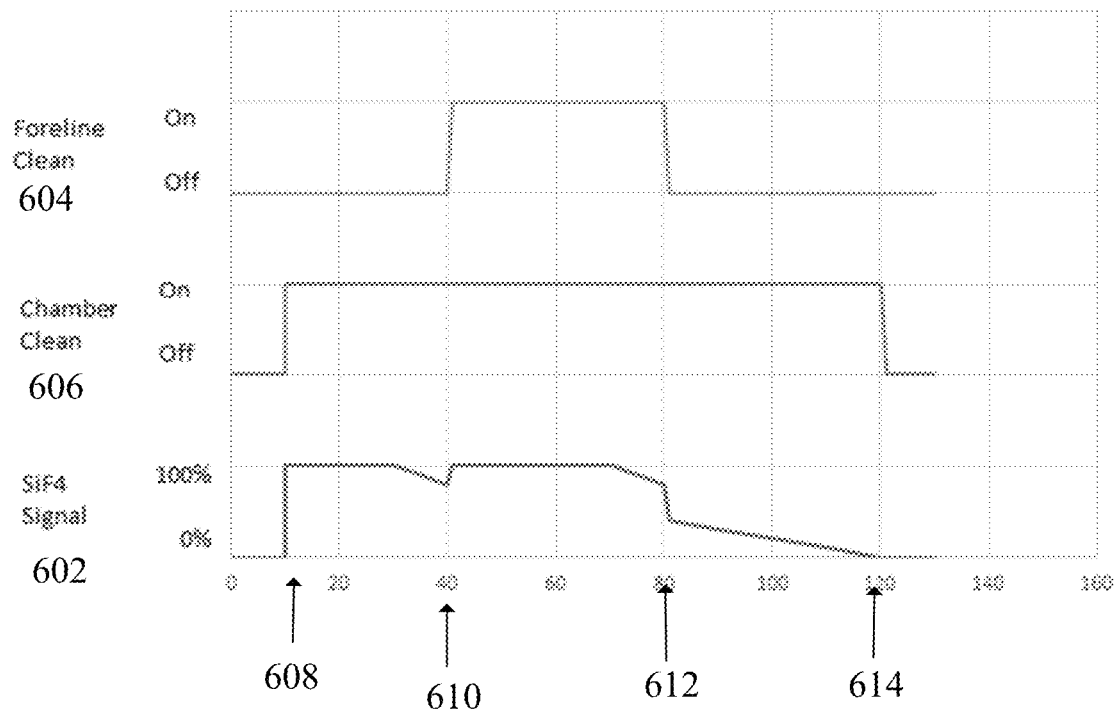
FIG. 6 shows another exemplary diagram of silicon tetrafluoride concentration measured by the endpoint detector of the processing system of FIG. 3, according to some embodiments of the present invention.

FIG. 6 shows another exemplary diagram of silicon tetrafluoride concentration 602 measured by the endpoint detector 312 of the processing system 300 of FIG. 3, according to some embodiments of the present invention. Specifically, the silicon tetrafluoride concentration 602 is measured over a duration 604 of a cleaning operation by the foreline cleaning source 306 and a duration 606 of a cleaning operation by the chamber cleaning source 304. Similar to the approach of FIG. 5, the chamber cleaning source 304 activates the chamber cleaning operation at a start time 608 (as reflected by the binary signal 606 at time 608) earlier than the start time 610 of activation of a pumping line cleaning operation by the foreline cleaning source 306 (as reflected by the binary signal 604 at time 610). The start of chamber cleaning at time 608 corresponds to a sharp rise in the partial pressure of $SiF_4$ detected by the endpoint detector 312, as reflected by the signal 602 at time 608. Further, in the approach of FIG. 6, the foreline cleaning source 306 is deactivated at an end time 612 (as reflected by the binary signal 604 at time 612) while chamber cleaning remains active. At this time 612, the concentration of $SiF_4$ remains above a predetermined endpoint threshold, which is about 0% in this case, as reflected by the signal 602 at time 612, thus indicating that chamber cleaning has not reached its endpoint. Therefore, chamber cleaning by the chamber cleaning source 304 remains active until the $SiF_4$ concentration measured at the detector 312 decays to the predetermined endpoint threshold of 0% at time 614, as reflected by the signal 602 at time 614. As shown, chamber cleaning is not affected by the termination of pumping line cleaning at the earlier time 612.

In this approach, the downstream endpoint detector 312 is adapted to accurately and timely detect the endpoint of cleaning of the processing chamber 302 when the foreline cleaning source 306 is deactivated prior to the chamber cleaning source 304 and before the endpoint threshold is reached. In some embodiments, a single system signal controls activation and deactivation of cleaning by both the chamber cleaning source 304 and the foreline cleaning source 306, in which case the foreline cleaning source 306 can be configured to deactivate itself after a given time period of operation, even when no central deactivation signal is received. The cleaning approaches described above with reference to FIGS. 5 and 6 show that pumping line cleaning can be started after chamber cleaning to minimize cleaning operation time of the foreline cleaning source 306, thereby extending its useful life. Moreover pumping line cleaning can be deactivated at the same time as the deactivation of chamber cleaning (shown in FIG. 5) or earlier than the deactivation chamber cleaning (as shown in FIG. 6). Such deactivation approaches are appropriate in situations where less extensive cleaning of the pumping line 308 is required.

Figure 7:
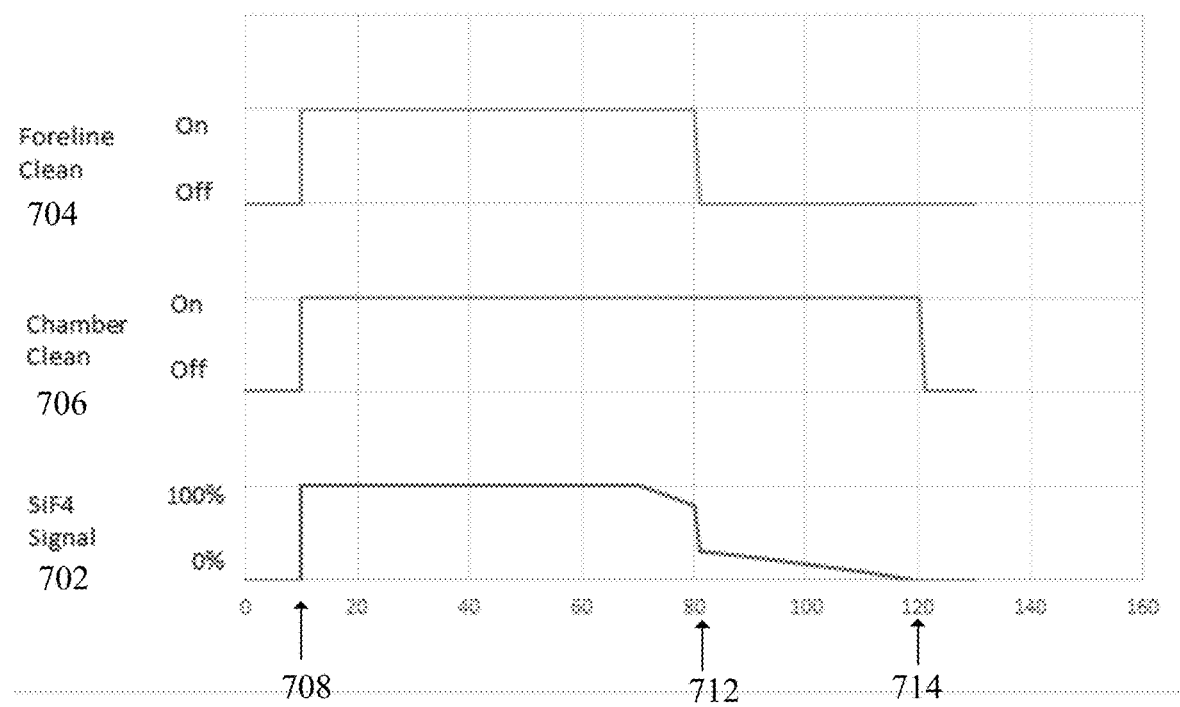
FIG. 7 shows another exemplary diagram of silicon tetrafluoride concentration measured by the endpoint detector of the processing system of FIG. 3, according to some embodiments of the present invention.

FIG. 7 shows yet another exemplary diagram of silicon tetrafluoride concentration 702 measured by the endpoint detector 312 of the processing system 300 of FIG. 3, according to some embodiments of the present invention. Specifically, the silicon tetrafluoride concentration 702 is measured over a duration 704 of a cleaning operation by the foreline cleaning source 306 and a duration 706 of a cleaning operation by the chamber cleaning source 304. The cleaning approach of FIG. 7 is similar to the approach of FIG. 6, except that the activation of the foreline cleaning source 306 is at about the same time as the activation of the chamber cleaning source 304, as reflected by binary signals 704 and 706 both being turned on at time 708. This cleaning approach is appropriate in cases where more extensive cleaning of the pumping line 308 is required. Similar to FIG. 6, the foreline cleaning source 306 is deactivated at an end time 712 (as reflected by signal 704 at time 712) while the chamber cleaning source 304 remains active, and the concentration of $SiF_4$ remains above a predetermined endpoint threshold, which is about 0% in this case, as reflected by the signal 702 at time 712. This indicates that chamber cleaning has not reached its endpoint. Therefore, chamber cleaning by the chamber cleaning source 304 remains active until the $SiF_4$ concentration measured at the detector 312 decays to the predetermined endpoint threshold of 0% at time 714, as reflected by the signal 702 at time 714. Again, chamber cleaning is not affected by the termination of pumping line cleaning at the earlier time 712. Further, the chamber cleaning source 304 can be deactivated at about time 714.

In another exemplary operation of the system 300 of FIG. 3 (not illustrated), the chamber cleaning source 304 is deactivated while pumping line cleaning by the foreline cleaning source 306 remains active and unaffected until the silicon tetrafluoride concentration decays to a predetermined threshold, thus representing the end of cleaning of the pumping line 308. In this approach, the downstream endpoint detector 312 is adapted to timely detect the endpoint of cleaning of the pumping line 308 when the chamber cleaning source 304 is deactivated prior to the foreline cleaning source 306. In some embodiments, a single system signal controls activation and deactivation of cleaning by both the chamber cleaning source 304 and the foreline cleaning source 306, in which case the chamber cleaning source 304 can be configured to deactivate itself after a given time period of operation, even when no central deactivation signal is received.

Figure 8:
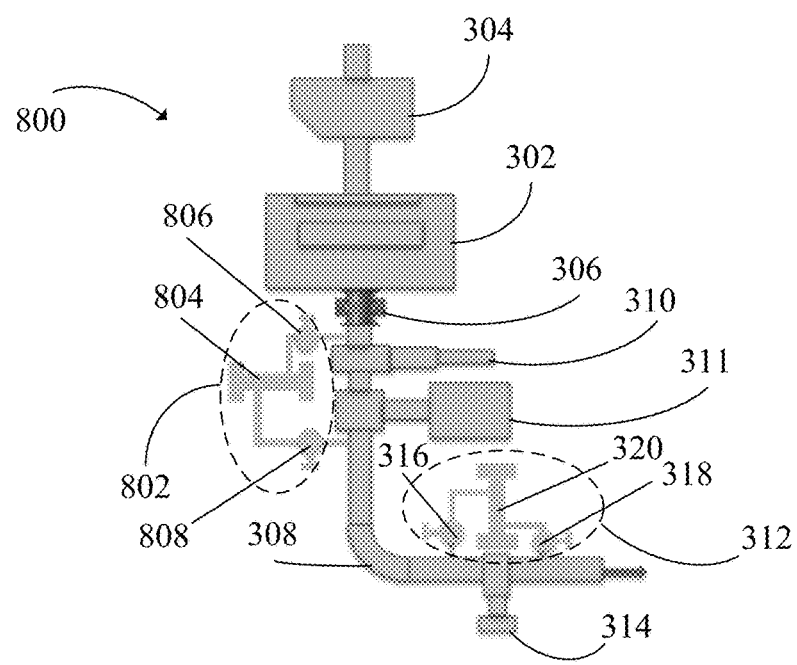
FIG. 8 shows another exemplary processing system with integrated chamber cleaning endpoint detection and pumping line cleaning endpoint detection, according to some embodiments of the present invention.

FIG. 8 shows another exemplary processing system 800 with integrated chamber cleaning endpoint detection and pumping line cleaning endpoint detection, according to some embodiments of the present invention. The configuration of the processing system 800 is similar to that of the processing system 300 of FIG. 3, except for the addition of an intermediate endpoint detector 802 in the system 800. As shown in FIG. 8, the intermediate endpoint detector 802 is coupled to the pumping line 308 downstream from the plasma chamber 302, the chamber cleaning source 304 and the foreline cleaning source 306, while upstream to the downstream endpoint detector 312. In some embodiments, the intermediate endpoint detector 802 is mounted on a bypass of the pumping line 308 and parallel to the gate valve 310 and the throttle valve 311. The intermediate endpoint detector 802 can have substantially the same configuration as the downstream endpoint detector 312, including a detection cell 804 sandwiched between a pair of isolation valves 806, 808. In some embodiments, the isolation valves 806, 808 can have the same function as isolation valves 316, 318 of the downstream endpoint detector 312 and the detection cell 804 can have the same function as the detection cell 320 of the downstream endpoint detector 312.

In some embodiments, the intermediate endpoint detector 802 is configured to determine the concentration of the signature chemical substance (e.g., $SIF_4$) in the gas flowing across its detection cell 804. In some embodiments, the measurements provided by the intermediate endpoint detector 802 is used to detect an endpoint of cleaning of the processing chamber 302. In some embodiments, the measurements provided by the downstream endpoint detector 312 is used to detect an endpoint of cleaning of the processing chamber 302 and/or the pumping line 308.

Figure 9:
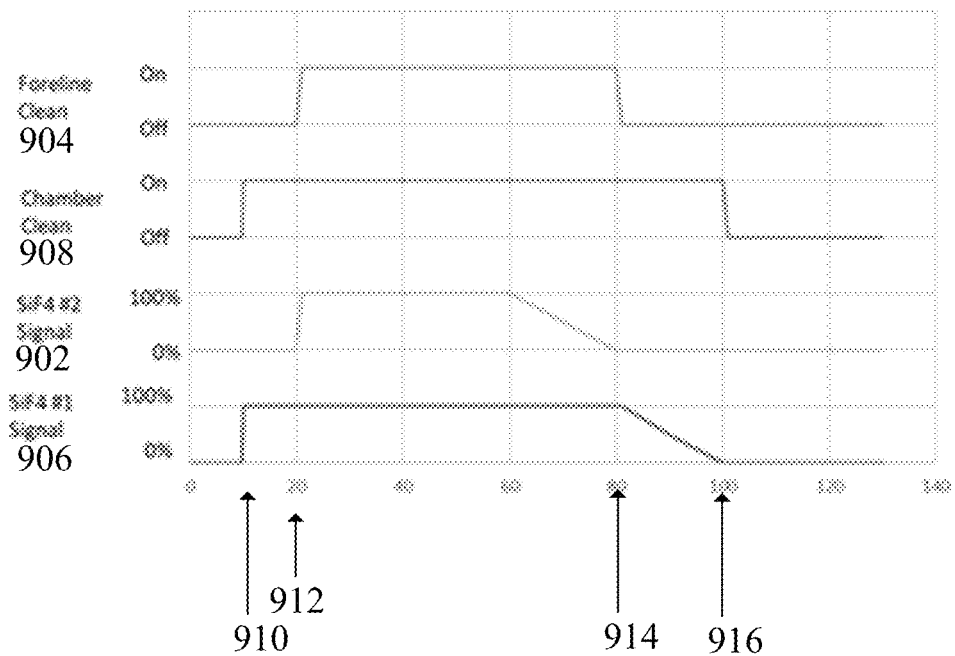
FIG. 9 shows an exemplary diagram of silicon tetrafluoride concentrations measured by the two endpoint detectors of the processing system of FIG. 8, according to some embodiments of the present invention.

FIG. 9 shows an exemplary diagram of silicon tetrafluoride concentrations measured by the two endpoint detectors 802, 312 of the processing system 800 of FIG. 8, according to some embodiments of the present invention. Specifically, FIG. 9 shows silicon tetrafluoride concentration 902 measured by the downstream endpoint detector 312 and silicon tetrafluoride concentration 906 measured by the intermediate endpoint detector 802 over a duration 904 of a cleaning operation by the foreline cleaning source 306 and a duration 908 of a cleaning operation by the chamber cleaning source 304.

In the exemplary cleaning operations illustrated in FIG. 9, the chamber cleaning source 304 is activated at time 910 to initiate a cleaning operation of the processing chamber 302, as reflected by the binary signal 908 being turned on at that time. At about the same time, the intermediate endpoint detector 802 detects a corresponding rise in the partial pressure of SiF4 generated by the cleaning of the processing chamber 302, as reflected by the signal 906 at time 910. The foreline cleaning source 306 is activated at a later time 912 relative to the activation time of the chamber cleaning source 304 to start cleaning of the pumping line 308, as reflected by the binary signal 904 being turned on at that time 912. At the same time, the downstream endpoint detector 312 can detect a corresponding rise in the partial pressure of SiF4 generated by the cleaning of both the pumping line 308 and the processing chamber 302, as reflected by the signal 906 at time 912. The pumping line cleaning operation by the foreline cleaning source 306 can be terminated at time 914, as reflected by the signal 904 being turned off at time 914, while chamber cleaning by the chamber cleaning source 304 remains active. At that time 914, the downstream endpoint detector 312 detects that the partial pressure of SiF4 at its location has decayed to around the predetermined endpoint threshold (e.g., 0%), as reflected by signal 902 at time 914, while the intermediate endpoint detector 802 detects that the partial pressure of SiF4 at its location remains above this level, as reflected by signal 906 at time 914. Thereafter, both the intermediate endpoint detector 802 and the downstream detector is able to detect the endpoint of cleaning of the processing chamber 302 at time 916, when the monitored SiF4 concentrations at both locations decay to and stabilize around the predetermined endpoint threshold of 0% partial pressure, as reflected by both signals 902 and 906 at time 916.

Figure 10:
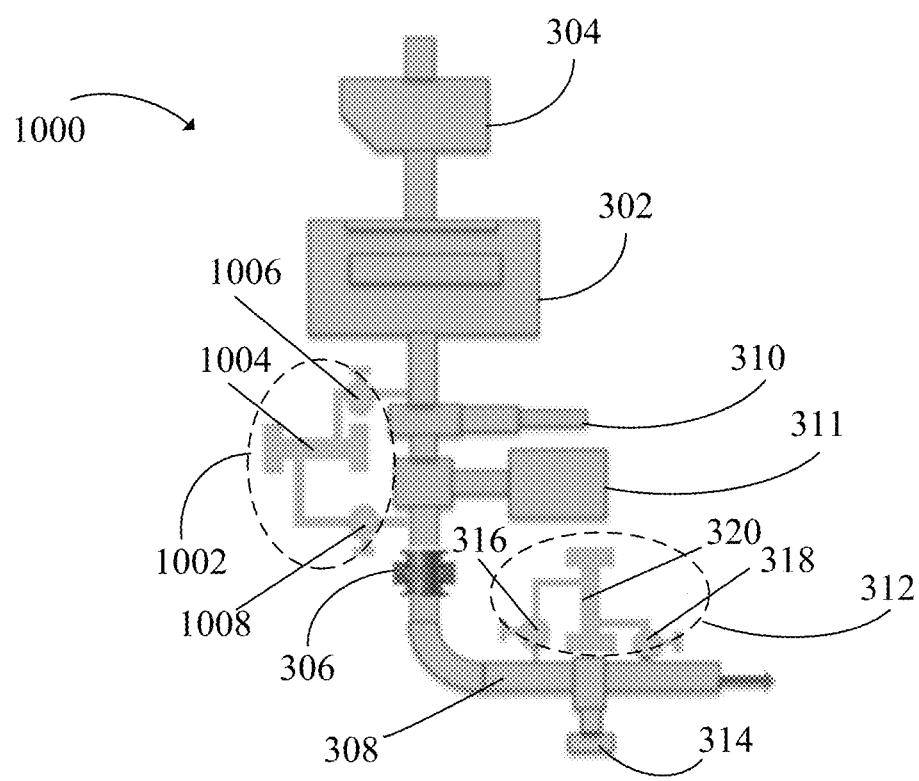
FIG. 10 shows yet another exemplary processing system with integrated chamber cleaning endpoint detection and pumping line cleaning endpoint detection, according to some embodiments of the present invention.

FIG. 10 shows yet another exemplary processing system 1000 with integrated chamber cleaning endpoint detection and pumping line cleaning endpoint detection, according to some embodiments of the present invention. The configuration of the processing system 1000 is similar to that of the processing system 300 of FIG. 3, except for the addition of an intermediate endpoint detector 1002 in the system 1000. The configuration of the processing system 1000 is different from the processing system 800 of FIG. 8 in that the intermediate endpoint detector 1002 is coupled to the pumping line 308 between the processing chamber 302 and the foreline cleaning source 306, that is, downstream from the processing chamber 302, but upstream to the foreline cleaning source 306. The intermediate endpoint detector 1002 is also upstream to the downstream endpoint detector 312. In some embodiments, the intermediate endpoint detector 1002 is mounted on a bypass of the pumping line 308 and parallel to the gate valve 310 and the throttle valve 311, which can also be upstream to the foreline cleaning source 306. The intermediate endpoint detector 1002 can have substantially the same configuration as the downstream endpoint detector 312, including a detection cell 1004 sandwiched between a pair of isolation valves 1006, 1008. In some embodiments, the isolation valves 1006, 1008 can have the same function as isolation valves 316, 318 of the downstream endpoint detector 312 and the detection cell 1004 can have the same function as the detection cell 320 of the downstream endpoint detector 312.

In some embodiments, the intermediate endpoint detector 1002 is configured to determine the concentration of the byproduct chemical substance (e.g., $SIF_4$) in the gas flowing across its detection cell 1004. In some embodiments, the measurements provided by the intermediate endpoint detector 1002 is used to detect an endpoint of cleaning of the processing chamber 302. In some embodiments, the measurements provided by the downstream endpoint detector 312 is used to detect an endpoint of cleaning of the processing chamber 302 and/or the pumping line 308.

Figure 11:
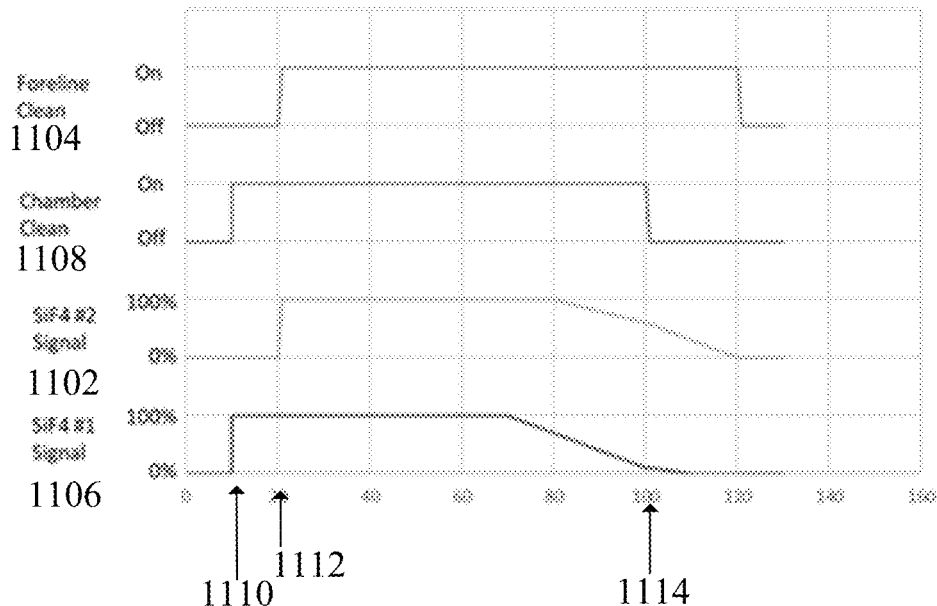
FIG. 11 shows an exemplary diagram of silicon tetrafluoride concentrations measured by the endpoint detectors of the processing system of FIG. 10, according to some embodiments of the present invention.

FIG. 11 shows an exemplary diagram of silicon tetrafluoride concentrations measured by the endpoint detectors 1002, 312 of the processing system 1000 of FIG. 10, according to some embodiments of the present invention. Specifically, FIG. 11 shows silicon tetrafluoride concentration 1102 measured by the downstream endpoint detector 312 and silicon tetrafluoride concentration 1106 measured by the intermediate endpoint detector 1002 over a duration 1104 of a cleaning operation by the foreline cleaning source 306 and a duration 1108 of a cleaning operation by the chamber cleaning source 304.

In the exemplary cleaning operations illustrated in FIG. 11, the chamber cleaning source 304 is activated at time 1110 to initiate a cleaning operation of the processing chamber 302, as reflected by the binary signal 1108 being turned on at that time. At about the same time, the intermediate endpoint detector 1002 detects a corresponding rise in the partial pressure of SiF4 generated by the cleaning of the processing chamber 302, as reflected by the signal 1106 at time 1110. Because the foreline cleaning source 306 is installed downstream from the intermediate endpoint detector 1002, activation of the foreline cleaning source 306 during a cleaning operation of the processing chamber 302 when the chamber cleaning source 304 is also activated does not interfere with the accurate monitoring and detection of the endpoint of cleaning of the processing chamber 302 by the intermediate endpoint detector 1002. Thus, the foreline cleaning source 306 can be activated at a time 1112 after the activation of the chamber cleaning source 304, but prior to the chamber cleaning source 304 being deactivated. This is reflected by the signal 1104 being turned on at the later time 1112. When the SiF4 concentration monitored by the intermediate endpoint detector 1002 decays to and stabilizes around a predetermined threshold level (e.g., 0% partial pressure) at time 1114, as reflected by the signal 1106 at time 1114, the endpoint of cleaning of the processing chamber 302 is detected. In some embodiments, the chamber cleaning operation is terminated at time 1114 by deactivating the chamber cleaning source 304, as reflected by the signal 1108 being turned off at time 1114.

To detect the endpoint of cleaning of the pumping line 308 when the foreline cleaning source 306 is activated during a cleaning session of the processing chamber 302, the difference in $SiF_4$ concentrations between the two endpoint detectors is used to determine the pumping line cleaning endpoint. For example, if the downstream endpoint detector 312 detects a higher $SIF_4$ concentration signal than that of the intermediate endpoint detector 1002, then the difference indicates that the cleaning operation of the pumping line 308 is still generating a byproduct in the form of the signature chemical substance SiF4. Therefore, pumping line cleaning is still ongoing. This is shown in FIG. 11 from about time 70 to about time 120, where the $SiF_4$ concentration 1102 measured by the downstream endpoint detector 312 is higher than the $SiF_4$ concentration 1106 measured by the intermediate detector 1002. If it is determined that the $SiF_4$ concentration measured by the downstream endpoint detector 312 is about the same as that measured by the intermediate endpoint detector 1002, then the endpoint of cleaning of the pumping line 308 is reached, as reflected at about time 120 and onward for the $SiF_4$ signals 1102 and 1106.

In some embodiments, a control circuit (not shown) is provided to automate the cleaning and/or detection approaches of the present invention. For example, the control circuit can automatically operate (i) cleaning of the processing chamber 302 by the chamber cleaning source 304, (ii) cleaning of the pumping line 308 by the foreline cleaning source 306, (iii) opening/closing of the valves 316, 318 of the downstream endpoint detector 312 for monitoring cleaning byproduct concentration over a specific duration, and/or (iv) opening/closing of the valves of the intermediate endpoint detector (detector 802 or 1002) for monitoring cleaning byproduct concentration over a specific duration. In some embodiments, the control circuit can transmit a single control signal to initiate the cleaning of the processing chamber 302 and the pumping line 308, in which case the foreline cleaning source 306 can include circuitry that delays activation of cleaning (e.g., plasma ignition) for some configurable time after receipt of the activation signal such that pumping line cleaning commences after the commencement of chamber cleaning. In some embodiments, the control circuit can transmit a single control signal to deactivate the cleaning of the processing chamber 302 and the pumping line 308, in which case the foreline cleaning source 306 or the chamber cleaning source 304 can include circuitry that sets the cleaning deactivation time after a specific period of operation regardless of when the deactivation signal is received. In some embodiments, such as for the cleaning approaches explained above in relation to FIGS. 5-7, 9 and 11, at least a portion of a duration of the cleaning of the pumping line 308 overlaps in time with at least a portion of a duration of the cleaning of the processing chamber 302. In alternative embodiments, the cleaning operations are carried out consecutively and there is no overlap in duration between a chamber cleaning operation and a pumping line cleaning operation. In some embodiments, the determination of the endpoint of chamber cleaning and/or the endpoint of pumping line cleaning is performed locally at the respective endpoint detector(s). Alternatively, such determination is made by the central control circuit (or another remote unit) based on the monitored data provided by the endpoint detector(s). In some embodiments, more than two endpoint detectors and/or more than two cleaning sources are implemented along the pumping line 108, where each cleaning source and/or endpoint detector is assigned to a specific section of the pumping line 108. This implementation can be useful in a processing environment where byproduct accumulation varies significantly along the length of a pumping line as well as highly dependent on the specific process and/or equipment.

Figure 12:
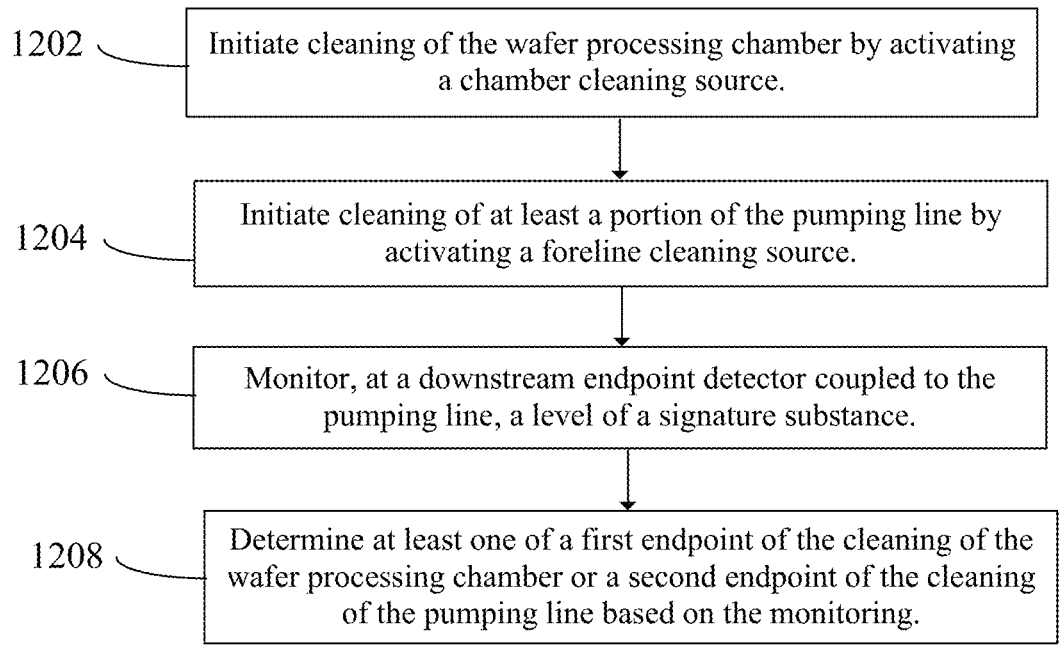
FIG. 12 shows an exemplary method for operating the processing systems of FIGS. 3, 8 and 10, according to some embodiments of the present invention.

FIG. 12 shows an exemplary method 1200 for operating the processing systems of FIGS. 3, 8 and 10, according to some embodiments of the present invention. As shown, the method 1200 starts with activation of the chamber cleaning source 304 to clean the processing chamber 302 (step 1202), followed by or at the same time as the activation of the foreline cleaning source 306 to clean the pumping line 308, where the foreline cleaning source 306 is generally located downstream from the processing chamber 302 and in fluid communication with the pumping line 308. In some embodiments, at least a portion of a duration of the cleaning of the pumping line 308 overlaps in time with at least a portion of a duration of the cleaning of the processing chamber 302. For example, to maximize cleaning efficiency of both cleaning operations, pumping line cleaning can start at the same time or later than chamber cleaning, and pumping line cleaning can end before or at the same time as chamber cleaning. The downstream endpoint detector 312, which is located downstream from the processing chamber 302 and the foreline cleaning source 306, can monitor one or both of the cleaning operations (step 1206). Specifically, the downstream endpoint detector 312 is configured to monitor a concentration level (e.g., partial pressure) of a signature chemical substance (e.g., $SiF_4$) that is generated as a product of the cleaning operations. Based on the measurements by the endpoint detector 312, one or both of the endpoints of chamber cleaning and pumping line cleaning can be detected when the $SiF_4$ concentration decays to and stabilizes around a predetermined endpoint threshold level (step 1208).

FIGS. 5-7 illustrate exemplary detection approaches when only one downstream endpoint detector 312 is present in the system. An optional second/intermediate endpoint detector can be present in the processing system, such as detector 802 in system 800 of FIG. 8 or detector 1002 in system 1000 of FIG. 10, where the intermediate endpoint detector is configured to detect the endpoint of cleaning of the processing chamber 302, while the downstream endpoint detector 312 can detect the endpoint of cleaning of the processing chamber 302 and/or the pumping line 308. In some embodiments, as illustrated in FIG. 8, the intermediate endpoint detector 802 is located downstream from the wafer processing chamber 302 and the foreline cleaning source 306, while upstream from the downstream endpoint detector 312. FIG. 9 illustrates an exemplary detection approach for the configuration of FIG. 8. In some embodiments, as illustrated in FIG. 10, the intermediate endpoint detector 1002 can be located downstream from the wafer processing chamber 302 while upstream from the foreline cleaning source 306 and the downstream endpoint detector 312. FIG. 11 illustrates an exemplary detection approach for the configuration of FIG. 10.

The present invention thus adds pumping line cleaning (e.g., by the foreline cleaning source 306) and diagnostic for and validation of the pumping line cleaning without adversely affecting chamber cleaning functionality or detection of chamber cleaning endpoint functionality. For example, the present invention enables time multiplexing of the endpoint detector(s) such that measurement of the byproduct chemical substance (e.g., $SiF_4$) generated from chamber cleaning can be differentiated from that generated from pumping line cleaning.

While the invention has been particularly shown and described with reference to specific embodiments, it should be understood by those skilled in the art that various changes in form and detail may be made therein without departing from the spirit and scope of the invention as defined by the appended claims.

What is claimed is:

1. A method for cleaning of a processing system comprising a wafer processing chamber and a pumping line in fluid connection with the wafer processing chamber and located downstream from the wafer processing chamber, the method comprising:
   initiating cleaning of the wafer processing chamber by activating a chamber cleaning source;
   initiating cleaning of at least a portion of the pumping line by activating a foreline cleaning source coupled to the pumping line, the foreline cleaning source located downstream from the wafer processing chamber, wherein at least a portion of a duration of the cleaning of the pumping line overlaps in time with at least a portion of a duration of the cleaning of the wafer processing chamber;
   monitoring, at a downstream endpoint detector coupled to the pumping line, a level of a signature substance that is a byproduct from the cleaning of at least one of the chamber or the pumping line, wherein a location of the downstream endpoint detector is downstream from both the wafer processing chamber and the foreline cleaning source;
   monitoring, at an intermediate endpoint detector coupled to the pumping line, a second level of the signature substance; and
   determining at least one of a first endpoint of the cleaning of the wafer processing chamber or a second endpoint of the cleaning of the pumping line based on at least one of the level of the byproduct signature substance monitored by the downstream endpoint detector or the second level of the signature substance monitored by the intermediate endpoint detector.

2. The method of claim 1, wherein a location of the intermediate endpoint detector is downstream from the wafer processing chamber while upstream from the foreline cleaning source and the downstream endpoint detector.

3. The method of claim 2, wherein the intermediate endpoint detector is adapted to detect the first endpoint of the wafer processing chamber cleaning based on the second level of the signature substance monitored.

4. The method of claim 3, wherein a difference between the level of the signature substance monitored by the downstream endpoint detector and the second level of the signature substance monitored by the intermediate endpoint detector is used to detect the second endpoint of the pumping line cleaning.

5. The method of claim 1, wherein the location of the intermediate endpoint detector is downstream from the wafer processing chamber and the foreline cleaning source, while upstream from the downstream endpoint detector.

6. The method of claim 5, further comprising deactivating the foreline cleaning source prior to monitoring by the intermediate endpoint detector to detect the first endpoint of the wafer processing chamber cleaning.

7. The method of claim 6, wherein the level of the signature substance monitored by the downstream endpoint detector is used to detect the second endpoint of the pumping line cleaning.

8. A method for cleaning of a processing system comprising a wafer processing chamber and a pumping line in fluid connection with the wafer processing chamber and located downstream from the wafer processing chamber, the method comprising:
   initiating cleaning of the wafer processing chamber by activating a chamber cleaning source;
   initiating cleaning of at least a portion of the pumping line by activating a foreline cleaning source coupled to the pumping line, the foreline cleaning source located downstream from the wafer processing chamber, wherein at least a portion of a duration of the cleaning of the pumping line overlaps in time with at least a portion of a duration of the cleaning of the wafer processing chamber;
   monitoring, at an intermediate endpoint detector coupled to the pumping line, a first level of a signature substance to determine a first endpoint of the cleaning of the wafer processing chamber, wherein a location of the intermediate endpoint is downstream from the wafer processing chamber; and
   monitoring, at a downstream endpoint detector coupled to the pumping line, a second level of the signature substance to determine a second endpoint of the cleaning of the pumping line, wherein a location of the downstream endpoint detector is downstream from the wafer processing chamber, the foreline cleaning source and the intermediate endpoint detector.

* * * * *